(12) United States Patent
Umezawa et al.

(10) Patent No.: US 10,181,307 B2
(45) Date of Patent: Jan. 15, 2019

(54) DISPLAY SYSTEM, EYEWEAR, AND METHOD FOR CONTROLLING DISPLAY SYSTEM

(71) Applicant: CANON KABUSHIKI KAISHA, Tokyo (JP)

(72) Inventors: Kohtaro Umezawa, Tokyo (JP); Takuro Miyasato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/406,528

(22) Filed: Jan. 13, 2017

(65) Prior Publication Data

US 2017/0206855 A1 Jul. 20, 2017

(30) Foreign Application Priority Data

Jan. 18, 2016 (JP) .................................. 2016-007424

(51) Int. Cl.

| G09G 5/02 | (2006.01) |
|---|---|
| A61F 9/02 | (2006.01) |
| G02C 11/00 | (2006.01) |
| G06F 1/16 | (2006.01) |
| G06F 3/01 | (2006.01) |
| G06F 3/0484 | (2013.01) |
| G09G 5/10 | (2006.01) |

(52) U.S. Cl.
CPC ............... *G09G 5/02* (2013.01); *A61F 9/022* (2013.01); *G02C 11/10* (2013.01); *G06F 1/163* (2013.01); *G06F 1/1637* (2013.01); *G06F 3/011* (2013.01); *G06F 3/04845* (2013.01); *G09G 5/10* (2013.01); *G09G 2320/0242* (2013.01); *G09G 2320/0626* (2013.01); *G09G 2320/0666* (2013.01); *G09G 2380/08* (2013.01)

(58) Field of Classification Search
CPC ........ G02B 1/00; G02B 27/01; G02B 27/017; G06F 17/30802; G06T 11/00; G06T 11/001; G06T 2200/16; H04N 1/387; H04N 1/60; H04N 1/64
USPC ......................................................... 345/594
See application file for complete search history.

(56) References Cited

U.S. PATENT DOCUMENTS

| 2009/0079757 A1* | 3/2009 | Kim ....................... G09G 5/003 345/604 |
|---|---|---|
| 2011/0012896 A1* | 1/2011 | Ji ....................... H04N 13/0429 345/419 |
| 2011/0216175 A1* | 9/2011 | Shimoyama ....... H04N 13/0438 348/56 |
| 2011/0261155 A1* | 10/2011 | Tsuruga ............. H04N 13/0051 348/43 |
| 2011/0305375 A1 | 12/2011 | Nelson |

(Continued)

FOREIGN PATENT DOCUMENTS

| CN | 103465825 A | 12/2013 |
|---|---|---|
| DE | 10354963 A1 | 7/2004 |

(Continued)

*Primary Examiner* — Sae Won Yoon
(74) *Attorney, Agent, or Firm* — Canon U.S.A., Inc. IP Division

(57) ABSTRACT

A display system comprises a display unit including a display screen, and a display control unit, wherein the display control unit sets at least one of luminance and a color map of the display screen based on wearing information indicating a wearing state of an eyewear.

21 Claims, 12 Drawing Sheets

(56) References Cited

U.S. PATENT DOCUMENTS

| | | | |
|---|---|---|---|
| 2013/0106820 A1* | 5/2013 | Seo | H04N 13/0438 |
| | | | 345/211 |
| 2014/0002475 A1* | 1/2014 | Oh | G06T 7/0012 |
| | | | 345/589 |
| 2014/0361955 A1 | 12/2014 | Goncalves | |
| 2016/0110846 A1* | 4/2016 | Park | G06T 5/00 |
| | | | 345/589 |
| 2016/0349507 A1* | 12/2016 | Hayashi | G02B 27/01 |

FOREIGN PATENT DOCUMENTS

| | | |
|---|---|---|
| DE | 102012106686 A1 | 5/2014 |
| EP | 2679159 A1 | 1/2014 |
| EP | 2698105 A2 | 2/2014 |
| JP | H07-124767 A | 5/1995 |
| WO | 2012107152 A1 | 8/2012 |

* cited by examiner

FIG.9
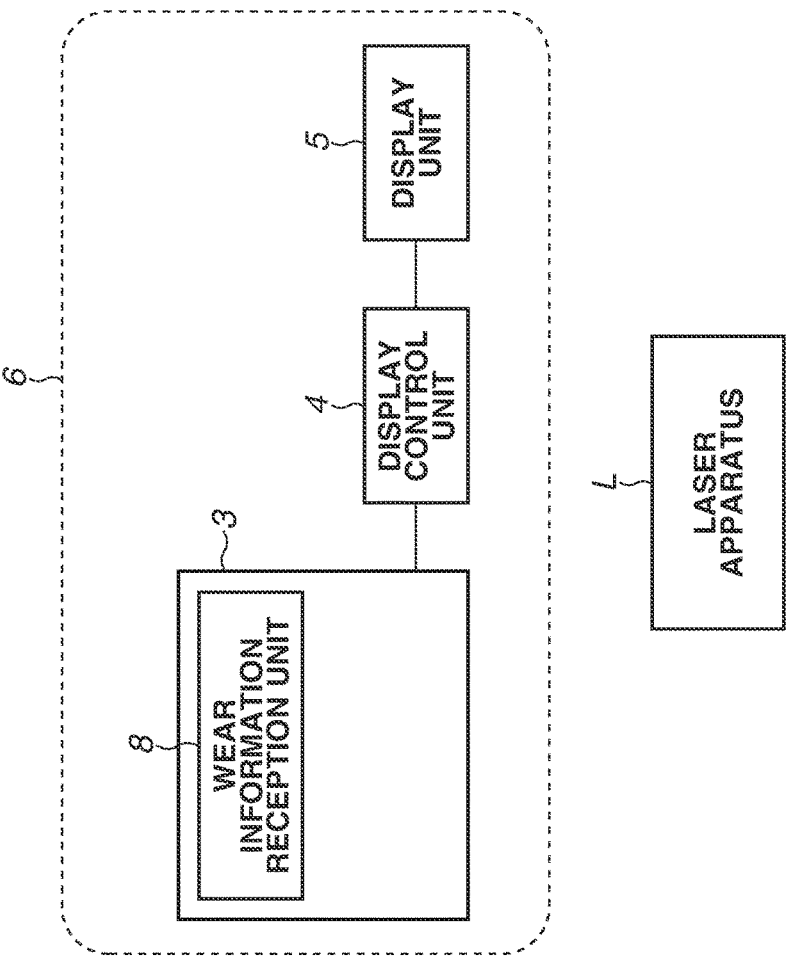
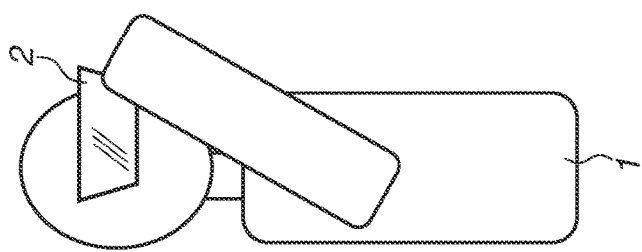

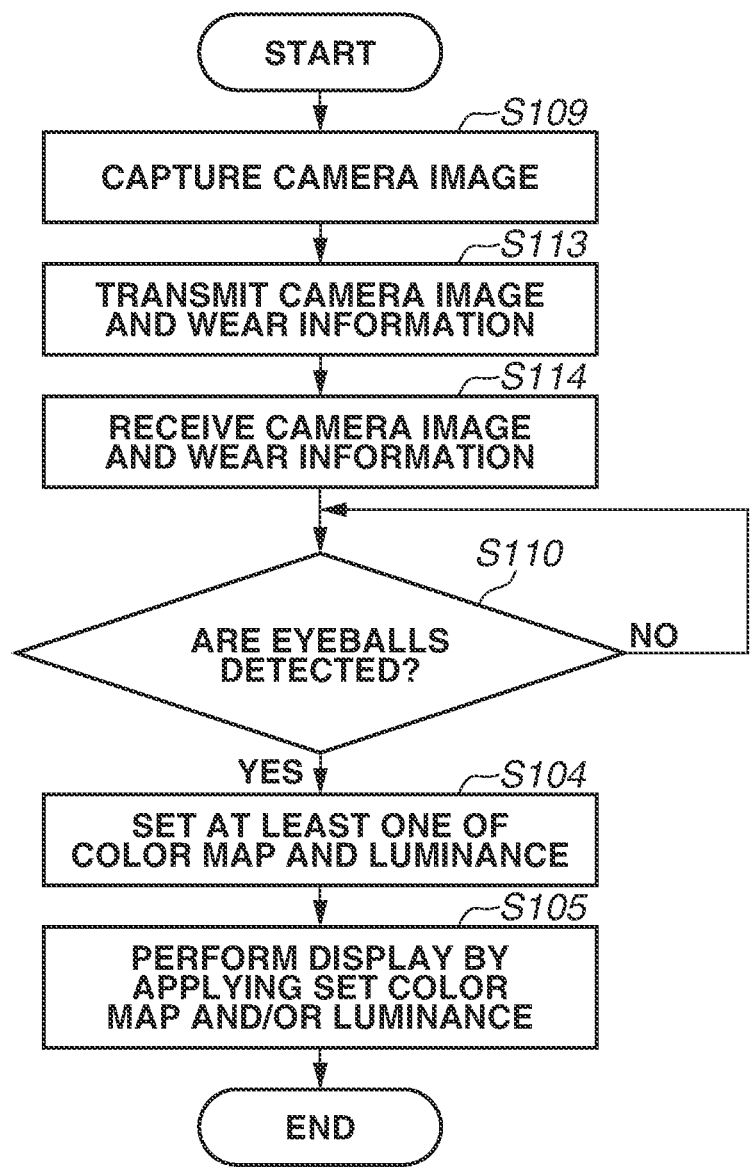

DISPLAY SYSTEM, EYEWEAR, AND METHOD FOR CONTROLLING DISPLAY SYSTEM

BACKGROUND OF THE INVENTION

Field of the Invention

The present disclosure relates to a display system, an eyewear, and a method for controlling a display system.

Description of the Related Art

Laser safety goggles, as wear for protecting eyes from direct light or scattered light from a laser when an apparatus for emitting high-intensity laser light is used, are known.

To prevent high-intensity laser light from being emitted to eyes, the laser safety goggles function to reduce the transmittance of light in some wavelength bands. Japanese Patent Application Laid-Open No. 7-124767 discusses in detail a handheld laser apparatus for emitting laser light that is used by a user while the user wears protective eyeglasses.

Generally, protective eyeglasses are colored to reduce not only the transmittance of some wavelength bands of laser light, but also the transmittance of some wavelength bands of visible light. In the state where an operator wears protective eyeglasses having colored lenses, the luminance of a display screen of a personal computer or a tablet terminal seems to be decreased to the operator, or it is difficult for the operator to view a user interface (UI) (e.g., a button) having a color similar to that of the lenses. In other words, the visibility of the display screen decreases for the operator. As a result, an error may occur in the operation of the UI.

SUMMARY OF THE INVENTION

The present disclosure is directed to a display system, an eyewear, and a method for controlling a display system that are capable of, in a case where an operator views a display screen in the state where the operator wears protective eyeglasses, reducing a decrease in the visibility occurring due to mixture of colors, and enabling the operator to easily operate a UI.

According to an aspect of the present disclosure, a display system has a display unit including a display screen, and a display control unit, wherein the display control unit sets at least one of luminance and a color map of the display screen based on wearing information indicating a wearing state of an eyewear.

According to another aspect of the present disclosure, an eyewear has a transmission unit configured to transmit wearing information indicating a wearing state of the eyewear worn by an operator.

According to yet another aspect of the present disclosure, a method for controlling a display system including a display unit, includes setting at least one of luminance and a color map of the display unit based on an input of wearing information indicating a wearing state of an eyewear.

Further features of the present disclosure will become apparent from the following description of exemplary embodiments with reference to the attached drawings.

BRIEF DESCRIPTION OF THE DRAWINGS

FIG. 9 is a schematic diagram illustrating a configuration of a display system according to an exemplary embodiment of the present disclosure.

FIG. 12 is a flowchart illustrating a processing flow performed by a display system according to an exemplary embodiment of the present disclosure.

DESCRIPTION OF THE EMBODIMENTS

Exemplary embodiments of the present disclosure will be described below with reference to the drawings. In principle, the same component is designated by the same numeral and is not described repeatedly.

The exemplary embodiments of the present disclosure will be described below. The exemplary embodiments described below are all merely illustrative, and do not limit the present disclosure. The exemplary embodiments described below may be changed in various manners without departing from the technical idea of the present disclosure. The present disclosure is not limited to a display system, and can also be carried out as a method for controlling a display system, and a program for executing the method.

In a first exemplary embodiment, a description is given of a laser system having a display system 6 and a laser apparatus L, of which the operation can be controlled by operating the display system 6.

(Overall Configuration of Apparatus)

In the first exemplary embodiment, if an operator presses an eyewear wearing button displayed on a user interface (UI) of a display system, the color map of the display system is changed to a color map corresponding to the color of an eyewear, thereby performing display. A description is given below taking, as an example of the eyewear, laser safety goggles having, as a colored light transmission portion, a colored lens that allows red light to pass therethrough. The description is given on the assumption that if information of the laser safety goggles is input to a mobile electronic tablet terminal, which is the display system according to the present exemplary embodiment, the color map of a display screen of the tablet terminal is changed according to the color of the light transmission portion of the laser safety goggles. In the specification, for convenience, in addition to the term "lens" being used to refer to a feature that can cause light to converge or a feature that can cause light to diverge, a lens that does not cause light to converge or diverge is also referred to as a "lens".

According to the present exemplary embodiment, even if an operator views a UI of a tablet terminal in the state where the operator wears an eyewear including a colored light transmission portion, such as laser safety goggles, it is possible to reduce a decrease in the visibility occurring due to the mixture of the color of the light transmission portion and the color of the UI. Consequently, the operator can easily operate the UI of the tablet terminal. Thus, it is possible to reduce an error in the operation.

Figure 1:
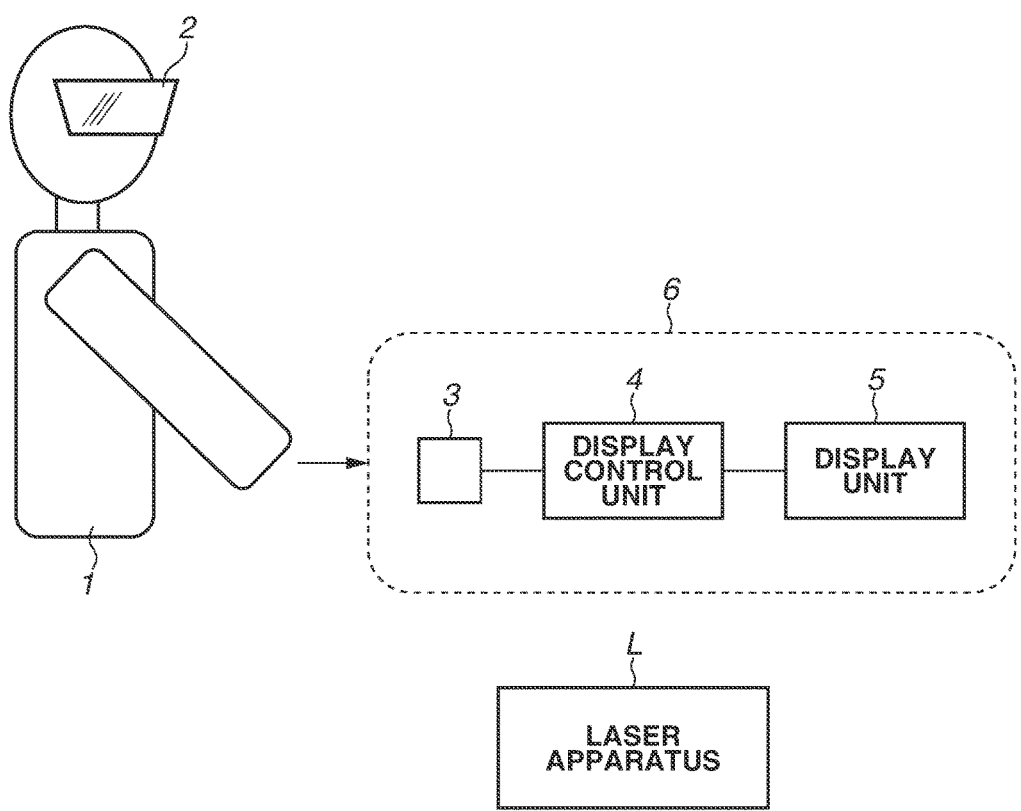
FIG. 1 is a schematic diagram illustrating a configuration of a display system according to an exemplary embodiment of the present disclosure.

FIG. 1 is a schematic diagram illustrating the configuration of the laser system according to the present exemplary embodiment. In FIG. 1, although not included in parts of the laser system and the display system 6, an operator 1 and an eyewear 2 are also illustrated in addition to the display system 6 and the laser apparatus L. The display system 6 according to the present exemplary embodiment has an information acquisition unit 3, a display control unit 4, and a display unit 5. If the operator 1 wears the eyewear 2 and inputs wearing information and color information of the eyewear 2 to the information acquisition unit 3, then based on the input information, the display control unit 4 changes a color map and updates a display screen displayed on the display unit 5.

Although not included in the display system 6, the eyewear 2 is related to the present exemplary embodiment and therefore is described in detail. It is desirable that the eyewear 2 should have the purpose of reducing the intensity of a particular band of a ray of light incident on eyes. The particular band may be set for the purpose of reducing the intensity of any band of light such as visible light, near-infrared light, or ultraviolet light. More specifically, the eyewear 2 is laser safety goggles, sunglasses, or a contact lens. The eyewear 2, however, is wear for achieving the above purpose, regardless of the form. Further, the eyewear 2 also corresponds to wear that changes (e.g., reduces or amplifies) the intensity of the band of part of a ray of light passing through the wear even if the wear does not achieve the above purpose. Further, colored film or colored glass that is not in the form of wear can also be equated with the eyewear 2. In this case, a display viewed through such film or glass by human eyes corresponds to the display system 6.

More specifically, examples of the assumed laser include various lasers such as a solid-state laser, a gas laser, a pigment laser, and a semiconductor laser. Particularly, a pulse laser such as a neodymium-doped yttrium aluminum garnet (Nd:YAG) laser or an alexandrite laser is more desirable. Alternatively, a titanium-sapphire (Ti:Sa) laser or an optical parametric oscillator (OPO) laser, which uses Nd:YAG laser light as excitation light, may be used. Yet alternatively, a light-emitting diode may be used instead of the laser. The light-emitting diode corresponds to lasers for various bands.

In the case of sunglasses, the eyewear 2 corresponds to a brown, black, or yellow lens or a photochromic lens. However, sunglasses in any other form may be used so long as the sunglasses reduce the intensity of a ray of light entering eyes. In the case of a contact lens, similarly, the eyewear 2 corresponds to a lens having a colored pupil portion. However, a contact lens in any other form may be used so long as the contact lens reduces the intensity of a ray of light entering eyes.

In the following description, the information acquisition unit 3, the display control unit 4, and the display unit 5 are described, and then, a processing flow is described with reference to FIG. 2. In the following description, unless otherwise stated, the color or color information of the eyewear 2 means the color or color information of a light transmission portion of the eyewear 2.

(Information Acquisition Unit 3)

The information acquisition unit 3 acquires wearing information and color information of the eyewear 2 that are input by the operator 1. Then, the information acquisition unit 3 transmits the acquired information to the display control unit 4. Examples of the wearing information include information indicating whether the eyewear 2 is worn. For example, a sensor for detecting whether the eyewear 2 is appropriately worn by the operator may be provided in the eyewear 2, and the detection result of the sensor may be transmitted as the wearing information to the display control unit 4.

It is desirable that the color information of the eyewear 2 should be transmission spectrum information of light remaining without being absorbed when white light passes through the eyewear 2. In a case where the eyewear 2 is laser safety goggles or sunglasses, it is desirable that the color information should be transmission spectrum information indicating the rate of change in the intensity of light in each frequency band incident on a light transmission portion of the laser safety goggles or the sunglasses.

The color information of the eyewear 2, however, may not only be transmission spectrum information, but also be the rate of change in the intensity of visible light at each wavelength passing through a partial area of the light transmission portion of the eyewear 2, or monochromatic red, green, and blue (RGB) color information of the light transmission portion. Further, a case has been described where the intensity of light in a particular band is reduced by light passing through a partial area of the eyewear 2. However, also in a case where the intensity of light in a particular band is increased by light passing through a partial area of the eyewear 2, transmission spectrum information or the rate of change in the intensity of visible light at each wavelength passing through the partial area of the light transmission portion of the eyewear 2 may be used. Alternatively, the color information may be information indicating the type of a light transmission portion or an eyewear. For example, identifications (IDs) associated with the types of eyewear are stored in a storage unit (not illustrated) of the display system 6, and information indicating the color of a light transmission portion or information of luminance or a color map to be applied is stored with respect to each of the IDs. Then, if an ID is acquired, and luminance or a color map corresponding to the acquired ID is selected, a similar function can be achieved.

The wearing information of the eyewear 2 may be information indicating whether the operator 1 using the display system 6 wears the eyewear 2. In the present exemplary embodiment, a description is given on the assumption that the single operator 1 inputs, to the display system 6, information indicating whether the operator 1 themselves wears the eyewear 2.

The information acquisition unit 3 may have a UI on a screen of an electronic tablet terminal, or a computer, a mouse, and a UI on a display in an apparatus including the computer, the mouse, and the display. The information acquisition unit 3 may be configured in such a manner that the operator 1 selects a button displayed on the display screen and to be pressed when the operator 1 wears laser safety goggles, or a button for selecting a color map to be changed.

(Display Control Unit 4)

The display control unit 4 stores a color map or luminance data to be used in the display unit 5. Then, based on information acquired by the information acquisition unit 3, the display control unit 4 transmits, to the display unit 5, information of a color map or luminance data to be applied.

As the color map to be used in the display unit 5, a color map may be created in advance with respect to each of the colors of light transmission portions in such a manner that the color map can maintain appropriate contrast with the color of the light transmission portion when the color map is mixed with the color. Then, the created color map may be stored in a storage unit (not illustrated). Alternatively, a color map may be created every time the operator 1 inputs the color of a light transmission portion.

It is desirable that the "color map" as used herein should be a color space, such as the hue, saturation, and value (HSV) color space, the hue, saturation, and lightness (HSL) color space, the RGB color space, or the cyan, magenta, and yellow (CMY) color space, calculated by the following method, using hue, saturation, and lightness, the three primary colors of color, or the three primary colors of light. Further, the color map may have a finite number of colors, such as 10 colors, 256 colors, or 10000 colors, extracted from these color spaces.

Figure 3:
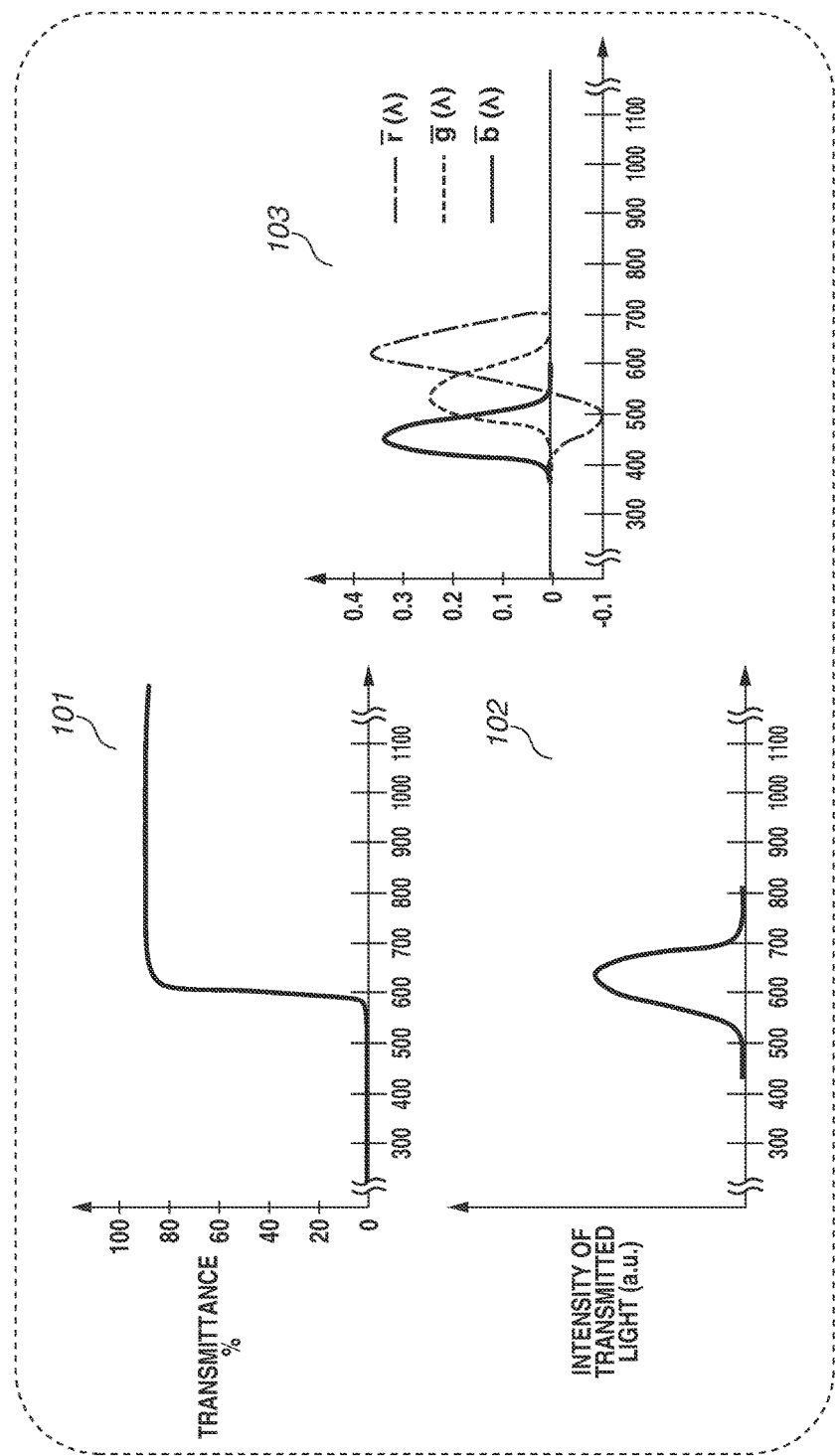
FIG. 3 illustrates graphs for illustrating a method for creating a color map according to an exemplary embodiment of the present disclosure.

With reference to FIG. 3, an example of a method for creating a color map is described. The description is given taking as an example a method for creating a color map for laser safety goggles including a red colored lens of which the transmission spectrum is known.

First, the transmission spectrum of the colored lens of the laser safety goggles is acquired. The transmission spectrum may be acquired from the specification of the goggles or acquired using the result of the operator 1 themselves measuring the spectrum. A case is considered where the transmission spectrum is acquired from the specification. According to a transmission spectrum 101 of the colored lens in this example, the transmittance of light from ultraviolet to about 600 nm is almost 0%. Next, the HSV color space represented by a conical model is divided into a finite number of, e.g., 1000, areas, and the representative colors of these areas are determined. It is more desirable that as a method for determining the representative colors, the color of the center of each area should be acquired. Alternatively, each area may be converted into coordinates, and the color of the point of the average value of the coordinates may be acquired. Yet alternatively, any method may be used. Then, the spectrum of each color is obtained and multiplied by the transmission spectrum of the colored lens, thereby calculating product spectrum distribution T(λ). A schematic diagram illustrates a spectrum 102 of a certain color in the HSV color space represented by a conical model. When the spectra are multiplied, the calculation is made according to formula 1, using spectrum intensity S(λ) at a wavelength λ and transmission spectrum intensity M(λ) of the colored lens. A product spectrum is calculated with respect to each wavelength λ, whereby it is possible to obtain the product spectrum distribution T(λ).

[Math. 1]

$$T(\lambda)=S(\lambda)\cdot M(\lambda) \qquad \text{formula (1)}$$

Then, the calculated product spectrum distribution T(λ) is multiplied by each of the International Commission on Illumination (CIE) 1931 RGB color-matching functions and the CIE standard color-matching functions, thereby recalculating colors in the HSV color space. Thus, it is possible to create, from the colors in the HSV color space represented by a conical model, a color map taking into account the transmission spectrum of the colored lens and having, for example, 1000 colors in the HSV color space. In FIG. 3, a graph illustrates the CIE 1931 RGB color-matching functions 103. In this manner, a color map can be created.

A case has been described where a color map is created without taking into account the light emission spectrum of a display to be used. In actuality, however, the appearance of the colors in the color map changes also depending on the light emission spectrum of the display to be used. In response, in formula 1, the spectrum intensity S(λ) at the wavelength λ may be separated into RGB elements of the display to be used. Then, each RGB element may be multiplied by the transmission spectrum of the lens, and a spectrum obtained from the sum of the resulting RGB elements may be the product spectrum distribution T(λ). Alternatively, the product spectrum distribution T(λ) can also be obtained by multiplying a light emission spectrum D(λ) of the display at the wavelength λ by the spectrum intensity S(λ) of each color and the transmission spectrum of the colored lens according to formula 2. It is assumed that the light emission spectrum of the display is stored in advance in the display control unit 4. Further, the calculated product spectrum distribution T(λ) is multiplied by each of the CIE 1931 RGB color-matching functions and the CIE standard color-matching functions, whereby it is possible to create, from the colors in the HSV color space represented by a conical model, a color map taking into account the transmission spectrum of the colored lens and having 1000 colors in the HSV color space.

[Math. 2]

$$T(\lambda)=D(\lambda)\cdot S(\lambda)\cdot M(\lambda) \qquad \text{formula (2)}$$

Further, in this case, the color contrast between any two points in the color space of the color map obtained by the above method may be calculated. Then, a color having a particular value as color contrast with a single color, a color having a particular value or more as color contrast with a single color, or a color having the greatest color contrast with a single color may be calculated and stored. Color contrast C is calculated according to the following formula 3. At this time, a point in the HSV color space is converted into that in the CIELAB color space.

[Math. 3]

$$C = \frac{|Q-P|}{|Q|+|P|} \qquad \text{formula (3)}$$

In this manner, it is possible to calculate a color map of the HSV color space by reflecting the light emission spectrum of the display or the transmission spectrum of the colored lens on the normal HSV color space. Further, it is also possible to calculate a color map having the greatest color contrast with each of these colors, and a map in which the color contrast of a single color with each of other colors is calculated. If the map in which the color contrast of a single color with each of other colors is calculated is used, it is also possible to create a color map using only a finite number of colors each having appropriate color contrast in the color map of the HSV color space obtained by reflecting the light emission spectrum of the display or the transmission spectrum of the colored lens on the normal HSV color space.

Alternatively, the light emission spectrum of the display or the CIE standard color-matching functions may be omitted, and a color map may be calculated by reflecting only the transmission spectrum of the colored lens on the normal HSV color space. Yet alternatively, any other method may be used.

Further, in the above example, a color map is created using the HSV color space. Alternatively, first, a color map may be calculated using the colors in the RGB space, and then, lightness corresponding to white to black may be added to the color map. Yet alternatively, a color map may be calculated using only the hue channel of the HSV space, and then, saturation or lightness may be added to the color map.

A color map has been created taking into account spectrum distribution, using the light emission spectrum of the display and the spectrum distribution of the laser safety goggles. The spectrum distribution of the colored lens of the laser safety goggles, however, may not necessarily need to be used. The color of the laser safety goggles measured in advance and represented by RGB may be used, and a color map of the HSV color space obtained by reflecting the color of the goggles and the light emission spectrum of the display on the normal HSV color space may be calculated using subtractive color mixture. Further, a color map having the greatest color contrast with each of these colors may be calculated.

When a color map is created, some colors are different in the RGB color space, but are the same in a color map taking into account the light emission spectrum of the display or the spectrum distribution of the laser safety goggles. In such a case, the same colors may be removed from the number of colors created as the same colors in a color map including a finite number of colors, thereby creating a color map including the number of colors reduced from the number of colors in the original HSV color space. Alternatively, a color map may be created using only a finite number of colors each having appropriate color contrast in the color map of the HSV color space taking into account the light emission spectrum of the display or the color of the goggles.

Using the thus calculated color map, the color of each button on a UI, the color of characters on the button, and the colors used in an image display portion in the display are determined. In this case, a color map having 100 colors is created using only a finite number of colors each having appropriate color contrast in the color map of the HSV color space taking into account the light emission spectrum of the display or the transmission spectrum of the colored lens. Then, for example, among these 100 colors, a color having the smallest color contrast with the color of the colored lens is determined as a background color, and a color having moderate color contrast with the color of the colored lens is determined as the color of a UI button. Thus, it is possible to determine the color of each button on a UI, the color of characters on the button, and the colors used in an image display portion in the display.

Further, using two colors having the greatest color contrast in such a color map, a finite number of colors or 256 colors in which there is a gradation between a certain color and another color such as in the grayscale of normal monochrome display may be created and stored, and an image may be displayed.

The luminance is the brightness of each portion of the display. In the present exemplary embodiment, it is assumed that in a case where the luminance is changed, the luminance of the entirety of the display is changed. The present disclosure, however, is not limited to this. Alternatively, the rate of change in the luminance of each area (a UI button or an image display portion) of the display may be changed.

To determine the luminance of the display when wear is worn, the average transmission intensity rate of a ray of light in the visible light region may be calculated based on the specification of the wear itself, and the current luminance may be multiplied by the multiplicative inverse of the average transmission intensity rate. For example, the average transmission intensity rate of a ray of light is set as a value from 0 to 1 in such a manner that 1 corresponds to a case where the ray of light completely passes through the wear. Further, the color map and the luminance may not be simultaneously set, and at least one of the color map and the luminance may be set according to information of the laser safety goggles.

(Display Unit 5)

The display unit 5 displays information using a color map set by the display control unit 4.

It is further beneficial that the display unit 5 is configured having an information processing apparatus and a display. The display may be a touch panel, or may not include an input mechanism such as a touch panel. In the case of a touch panel, the display unit 5 may include the information acquisition unit 3 and the display control unit 4.

As the display, a display such as a liquid crystal display (LCD), a cathode ray tube (CRT), or an organic electroluminescent (EL) display can be used. Each of these displays may have an input method such as a touch panel display.

As each of the information acquisition unit 3, the display control unit 4, and the display unit 5, a circuit generally termed a data acquisition system (DAS) and a processor such as a central processing unit (CPU), a microprocessor unit (MPU), or a graphics processing unit (GPU) can be used. Each unit may have a single processor or a single arithmetic circuit, or may have a plurality of processors or a plurality of arithmetic circuits.

Further, the display unit 5 may comprise a memory for storing data output from the information acquisition unit 3 and the display control unit 4. Typically, the memory is configured having a storage medium such as a read-only memory (ROM), a random-access memory (RAM), or a hard disk. The memory may be configured having one or more storage medium. The memory may be configured having one or more storage media such as ROMs, RAMS, and hard disks.

Figure 4:
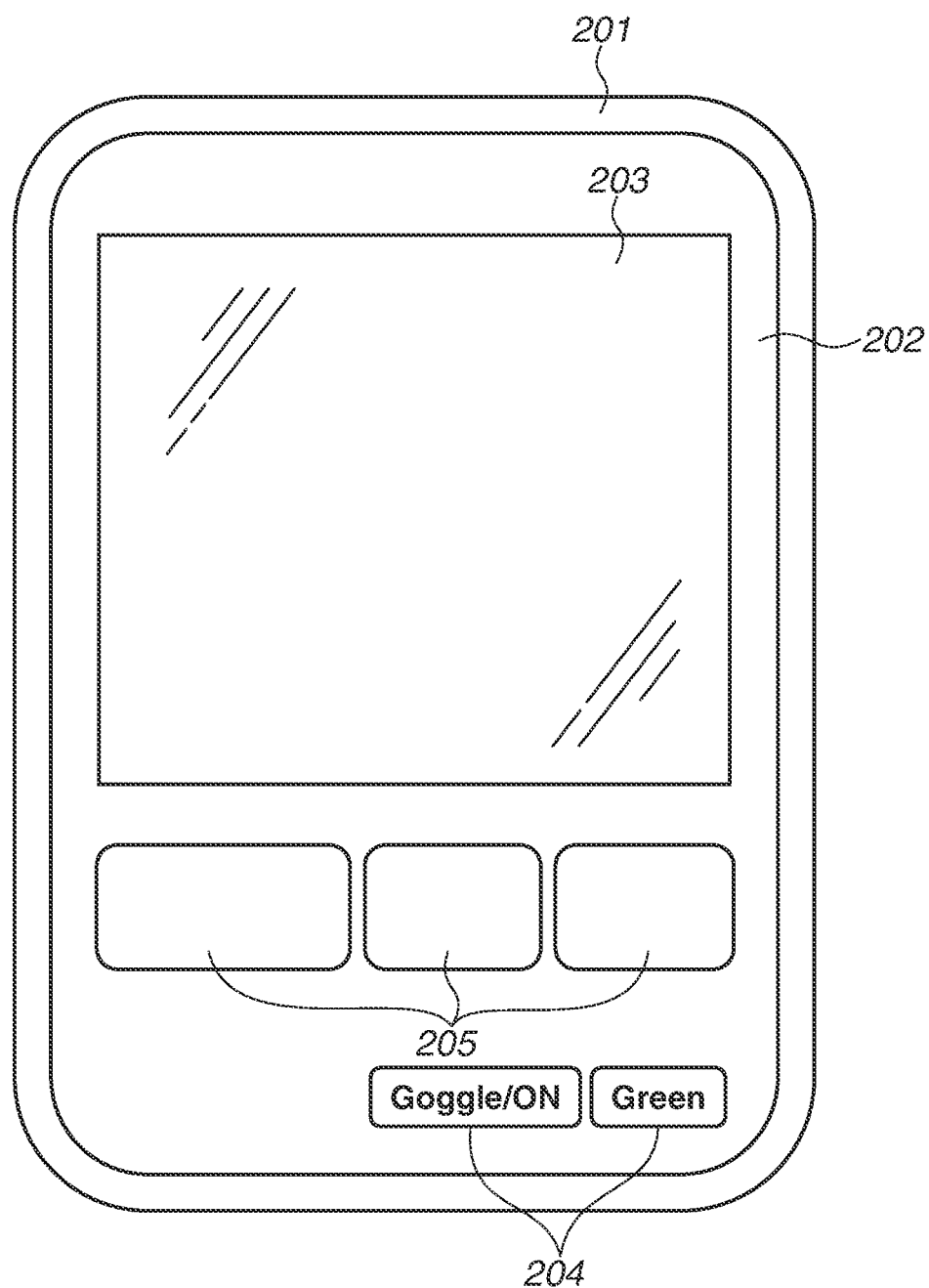
FIG. 4 is a schematic diagram illustrating a configuration of a display system according to an exemplary embodiment of the present disclosure.

With reference to FIG. 4, the information acquisition unit 3, the display control unit 4, and the display unit 5 are described on the assumption that the display system 6 is a tablet terminal. In FIG. 4, a tablet terminal 201 corresponds to the display system 6. A touch panel display unit 202 corresponds to the display unit 5 according to the present exemplary embodiment. The display unit 202 can display an image display area 203, a UI 204, which corresponds to the information input unit 3, and other UIs 205. In two buttons included in the UI 204, a button on the left side is a button for setting whether laser safety goggles are worn. A button on the right side is a button for selecting the color of a colored lens of laser safety goggles worn by the operator 1. A UI button 205 other than the above UIs 205 may be displayed. When the operator 1 wears laser safety goggles, and if the operator 1 presses the buttons 204, then according to the settings of the buttons 204, the display control unit 4 sets a color map for the UI buttons 204, the color of characters on the UI buttons 204, an image display portion, and other areas and transmits information of the color map to the display unit 5. Consequently, it is possible to make the visibility less likely to decrease even in the state where the operator 1 wears laser safety goggles.

As described above, the display control unit 4 sets at least one of the color map and the luminance based on wearing information of laser safety goggles, thereby reducing a decrease in the visibility. In addition to this, the display control unit 4 accentuates a character string on a UI, whereby it is possible to improve the visibility. For example, in FIG. 4, in the state where the operator 1 wears laser safety goggles, a character string such as "Goggle/ON" is displayed on a button. In the state where the operator 1 does not wear goggles, a character string such as "Goggle/OFF" is displayed on the button. At this time, when the operator 1 wears goggles, the field of view of the operator 1 is dark. Thus, the character string displayed on the button is made bolder, or the font size of the character string is made larger, than when the operator 1 does not wear goggles. Thus, it is possible to make it easy for the operator 1 to recognize the character string on the button even in the state where the operator 1 wears goggles.

Similarly to other configurations, the UIs are not limited to those illustrated in FIG. 4. For example, in an initial state, the UI 204 illustrated in FIG. 4 may be set so that a button for inputting color information is not displayed or cannot be operated. Then, according to an input indicating that laser safety goggles are worn, the button may be displayed, or the operation of the button may be permitted. Alternatively, only a button for inputting color information may be displayed, thereby representing whether goggles are worn. In this case, if goggles are not worn, characters "OFF" may be displayed. If goggles are worn, characters indicating the color of the goggles, such as "Orange", may be displayed, thereby indicating that a color map corresponding to orange goggles is set. Alternatively, any method may be employed so long as the method represents in an understandable manner the state where the color map is changed. When a laser safety goggle wearing button is pressed, a plurality of colors corresponding to laser safety goggles may pop up in the form of a list on a screen and may be able to be selected.

Further, according to the fact that information indicating that laser safety goggles are worn is input using the "Goggle/ON" button, a process other than the process of changing the luminance of display or the color map may be performed. For example, according to the fact that "Goggle/ON" is pressed, the laser apparatus L may be enabled to emit laser light or enabled to start measurement. More specifically, a signal permitting the emission of laser light from a laser light source is transmitted, or a signal permitting the start of measurement is transmitted.

The present exemplary embodiment employs the following form. A laser safety goggle wearing state selection button and a color map selection button are displayed side by side on the display. Then, when the laser safety goggle wearing state selection button is pressed, a plurality of goggle colors are displayed in the form of a list as the color map selection button.

(Laser Apparatus L)

The laser apparatus L is an apparatus that can be operated by the operator 1 through the display system 6. Specifically, the laser apparatus L is configured as a laser light source or a measuring apparatus using laser light emitted from a laser light source. As the measuring apparatus using laser light, a photoacoustic apparatus is known. The photoacoustic apparatus is an apparatus capable of, based on an acoustic wave generated by emitting pulse light to a specimen, visualizing the interior of the specimen. In a case where the photoacoustic apparatus is used in conjunction with the display system 6 according to the present exemplary embodiment, the photoacoustic apparatus may be configured to be controlled via the display system 6 to permit the emission of laser light used as the light source of pulse light to a specimen, or start or stop a measurement process.

(Processing Flow)

Next, the processing flow of the display system according to the present exemplary embodiment is described. FIG. 2 is a flowchart illustrating a processing flow according to the present exemplary embodiment.

In step S101, the display unit 5 displays the UI 204 illustrated in FIG. 4. Consequently, the display system 6 prompts the operator 1 to input information about the wearing state of laser safety goggles and the color of a colored lens.

In step S102, the wearing information acquisition unit 3 determines whether information indicating the wearing state of the goggles is input. If the goggle wearing state selection button is pressed (YES in step S102), the processing proceeds to step S103. If not (NO in step S102), step S102 is repeated, and the wearing information acquisition unit 3 waits for the goggle wearing state selection button to be pressed.

In step S103, the wearing information acquisition unit 3 determines whether information about the color of the light transmission portion of the laser safety goggles is input. If the color information selection button is pressed, and the color information is input (YES in step S103), the processing proceeds to step S104. If not (NO in step S103), step S103 is repeated, and the wearing information acquisition unit 3 waits for the color information to be input.

In step S104, according to the inputs in steps S102 and S103, the display control unit 4 sets at least one of the color map and the luminance.

In step S105, the display unit 5 performs display by applying the at least one of the color map and the luminance set in step S104.

Figure 2:
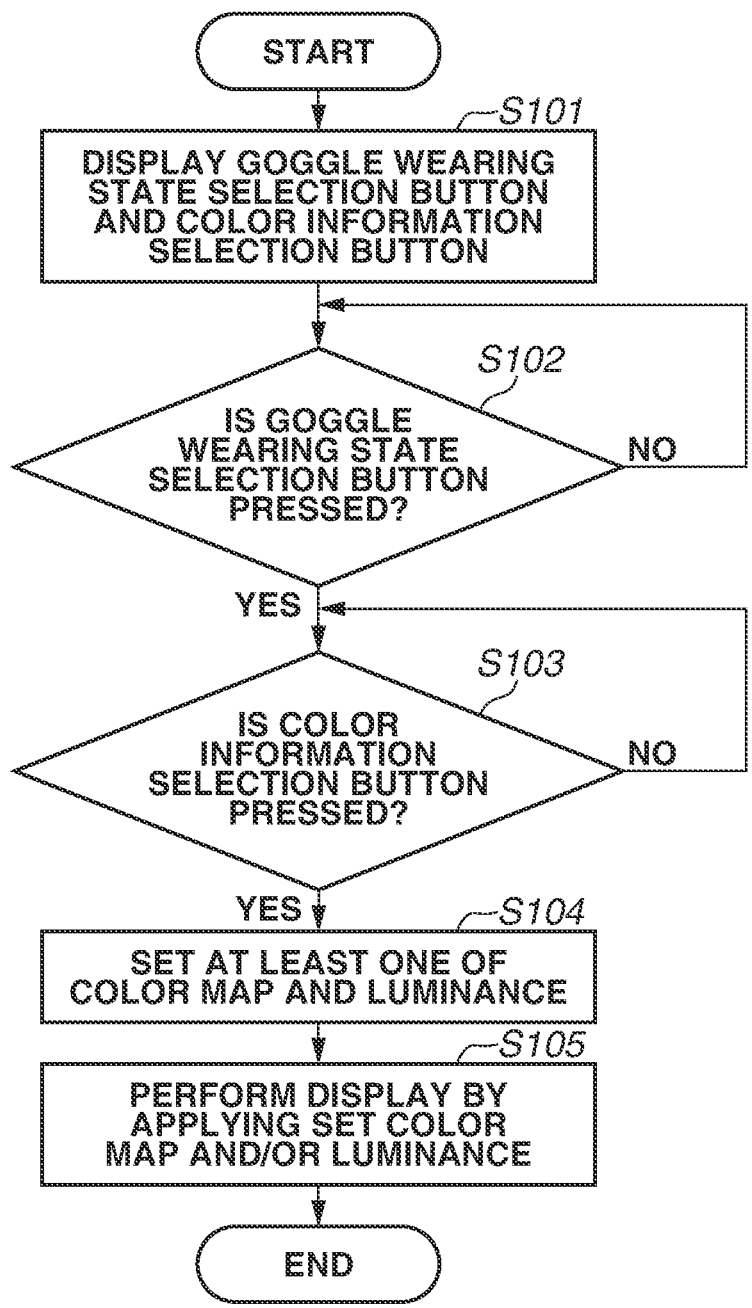
FIG. 2 is a flowchart illustrating a processing flow performed by a display system according to an exemplary embodiment of the present disclosure.

In the flow illustrated in FIG. 2, a case has been described where the color information selection button is displayed together with the goggle wearing state selection button in step S101. As described above, however, both buttons may not be simultaneously displayed in parallel. In this case, in step S101, only the goggle wearing state selection button may be displayed. Then, if the determination is YES in step S102, the color information selection button may be displayed before step S103.

Although not illustrated in FIG. 2, in a case where the operator 1 removes the laser safety goggles, the operator 1 can change back the settings of the UI 204 to the previous settings by operating the UI 204.

Further, in a case where the display system 6 is used in conjunction with the laser apparatus L, then after step S105, it is possible to display a button for permitting the emission of laser light and prompt the operator 1 to provide an input. Further, in a case where the laser apparatus L is a measuring apparatus such as a photoacoustic apparatus, then after step S105, it is possible to display a button for determining the start of measurement and prompt the operator 1 to provide an input.

Figure 5:
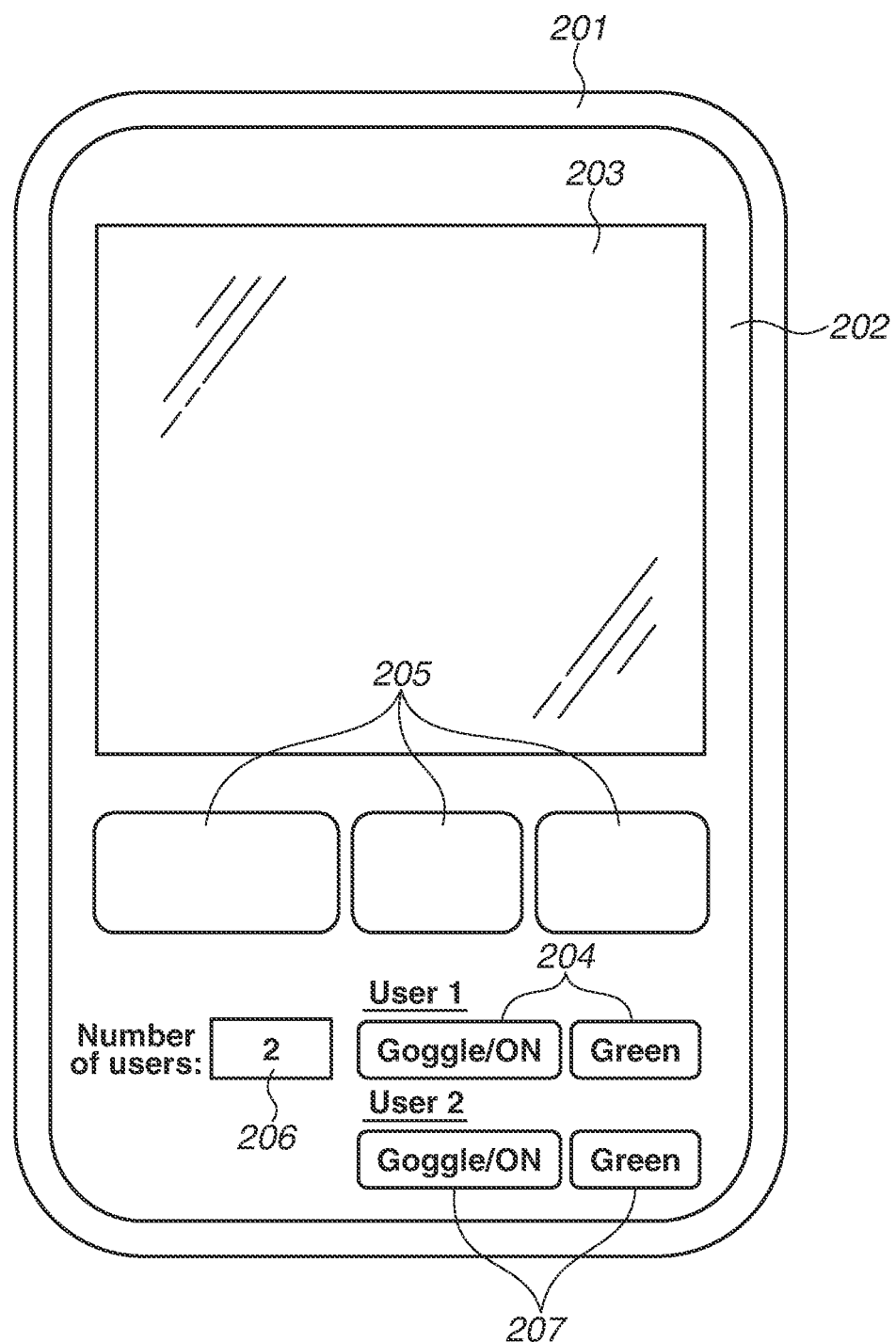
FIG. 5 is a schematic diagram illustrating a configuration of a display system according to an exemplary embodiment of the present disclosure.

Further, although a case has been assumed where only a single operator is present, there may also be a case where a plurality of operators are present, or a plurality of observers who observe the display system are present. In response, the display unit may display a UI for inputting the number of operators or observers who should confirm the wearing states of laser safety goggles, and all these operators or observers may be allowed to input the wearing states of the laser safety goggles. FIG. 5 illustrates an example of the display screen in this case.

The display screen illustrated in FIG. 5 is different from that in FIG. 4 in that a field 206 for inputting the number of (two in this case) operators or observers who should confirm the wearing state of laser safety goggles, and a UI 207 for inputting the wearing state and color information about the second operator or observer are displayed. The field 206 may be configured in such a manner that an operator can directly input a number using a keyboard or can make a selection from a list. On the UI 207, according to a value input to the field 206, buttons corresponding to the number of operators or observers are displayed. In a case where pieces of color information of laser safety goggles worn by a plurality of operators or observers are different from each other, then based on a synthetic transmission spectrum of the goggles based on the plurality of pieces of color information, at least one of the color map and the luminance is set. If an appropriate color map or appropriate luminance cannot be set for all the operators or observers, notification may be given to prompt the operators or observers to replace the laser safety goggles with laser safety goggles including a light transmission portion of another color.

As described above, in the present exemplary embodiment, when an operator presses a laser safety goggle wearing button, a list allowing the operator to select at least one of luminance and a color map according to the light emission spectrum of a display and the transmission spectrum of laser safety goggles is displayed. Then, it is possible to change display on the display using the at least one of the luminance and the color map according to the selection of the operator.

A more specific example of the present exemplary embodiment will be described below. In the present example, the eyewear 2 is laser safety goggles including a red light transmission portion. If information of the laser safety goggles is input to a mobile electronic tablet terminal as the display system 6, the color map of a display portion of the tablet terminal is changed according to the color of the laser safety goggles. In the present example, the luminance is not set.

First, the operator wears the red laser safety goggles and presses a laser safety goggle wearing state selection button displayed on the display of the tablet terminal. If the laser safety goggle wearing state selection button is pressed, a color map selection button is displayed as a list of a plurality of color maps. If one of the displayed color maps corresponding to the color of the laser safety goggles is selected, the color map of the display is changed, thereby performing display. A color map is created using the light emission spectrum of the display and the transmission spectrum of the laser safety goggles. The HSV color space is divided into 1000 colors. Each color is multiplied by the light emission spectrum of the display, the transmission spectrum of the goggles, and the CIE standard color-matching functions. The same colors are removed from the resulting color map to extract 100 colors. Using these 100 colors, the color of a UI of the display system and the color of an image display portion are determined.

Consequently, it is possible to provide a technique for, according to the fact that an operator presses an eyewear wearing state selection button displayed on a UI of a display system, changing the color map of the display system to a color map corresponding to the transmission spectrum of an eyewear, thereby performing display.

In this manner, when an operator wears an eyewear including a colored light transmission portion, such as laser safety goggles, and even if the operator views a UI of a tablet terminal through the light transmission portion, it is possible to reduce a decrease in the visibility occurring due to the mixture of colors and enable the operator to easily operate the UI of the tablet terminal.

Another example of the present exemplary embodiment will be described below. In the present example, the eyewear 2 is laser safety goggles including a red light transmission portion. If information indicating that the laser safety goggles are worn is input to a mobile electronic tablet terminal, the color map of a display portion of the tablet terminal is changed according to the color of the laser safety goggles. Further, in the present example, it is possible to control a photoacoustic imaging apparatus as a laser apparatus via the tablet terminal. Information indicating that the laser safety goggles are worn is input to the tablet terminal, whereby the photoacoustic imaging apparatus is enabled to emit laser light. In the present example, the luminance is not set.

In the present example, first, the operator wears the red laser safety goggles and presses a laser safety goggle wearing button displayed on the display of the tablet terminal. If the laser safety goggle wearing button is pressed, a color map selection button is displayed as a list of a plurality of color maps. If one of the displayed color maps corresponding to the color of the laser safety goggles is selected, the color map of the display is changed, thereby performing display. A color map is created using the light emission spectrum of the display and the transmission spectrum of the laser safety goggles. The HSV color space is divided into 1000 colors. Each color is multiplied by the light emission spectrum of the display, the transmission spectrum of the goggles, and the CIE standard color-matching functions. The same colors are removed from the resulting color map to extract 100 colors. Using these 100 colors, a color having high contrast with each of the 100 colors is calculated, and the color of a UI of the display system and the color of an image display portion are determined.

In the tablet terminal, the laser safety goggle wearing button is pressed, whereby a laser emission button is enabled to be pressed. This button is pressed, thereby starting the emission of laser light.

Consequently, it is possible to provide a technique for, if an operator presses an eyewear wearing button displayed on a UI of a display system, displaying a display screen by applying a color map corresponding to the color of an eyewear to the color map of the display system, and a technique for, according to the fact that an operator wears goggles, enabling the emission of laser light.

In this manner, when an operator wears a colored eyewear such as laser safety goggles, and even if the operator views a UI of a tablet terminal through a light transmission portion, it is possible to reduce a decrease in the visibility occurring due to the mixture of colors and enable the operator to easily operate the UI of the tablet terminal. Further, after it is confirmed that the laser safety goggles are worn, a laser apparatus is enabled to emit laser light.

A display system according to a second exemplary embodiment further has, in addition to the components of the first exemplary embodiment, an information acquisition unit for acquiring information of the eyewear. Only the differences from the first exemplary embodiment are described below.

In the first exemplary embodiment, the configuration has been described in which the operator 1 inputs the wearing state of the eyewear 2 to the information acquisition unit 3. In contrast, an information acquisition unit 3 according to the present exemplary embodiment has a wearing state detection unit. If an operator 1 wears the eyewear 2, then using a camera (a wearing state detection unit) provided in a display system 6, the information acquisition unit 3 detects that the operator 1 wears the eyewear 2. Then, the luminance and the color map of a display unit of the display system 6 are changed to those corresponding to the color of the eyewear 2, thereby performing display on the display unit. In the display system according to the present exemplary embodiment, the eyewear 2 is laser safety goggles including a green light transmission portion, and the display system 6 is a tablet terminal.

According to the present exemplary embodiment, in addition to effects similar to those of the first exemplary embodiment, even if an operator does not input, to the display system, information indicating that laser safety goggles are worn, it is possible to detect the wearing state of the laser safety goggles using a wearing information detection method.

Figure 6:
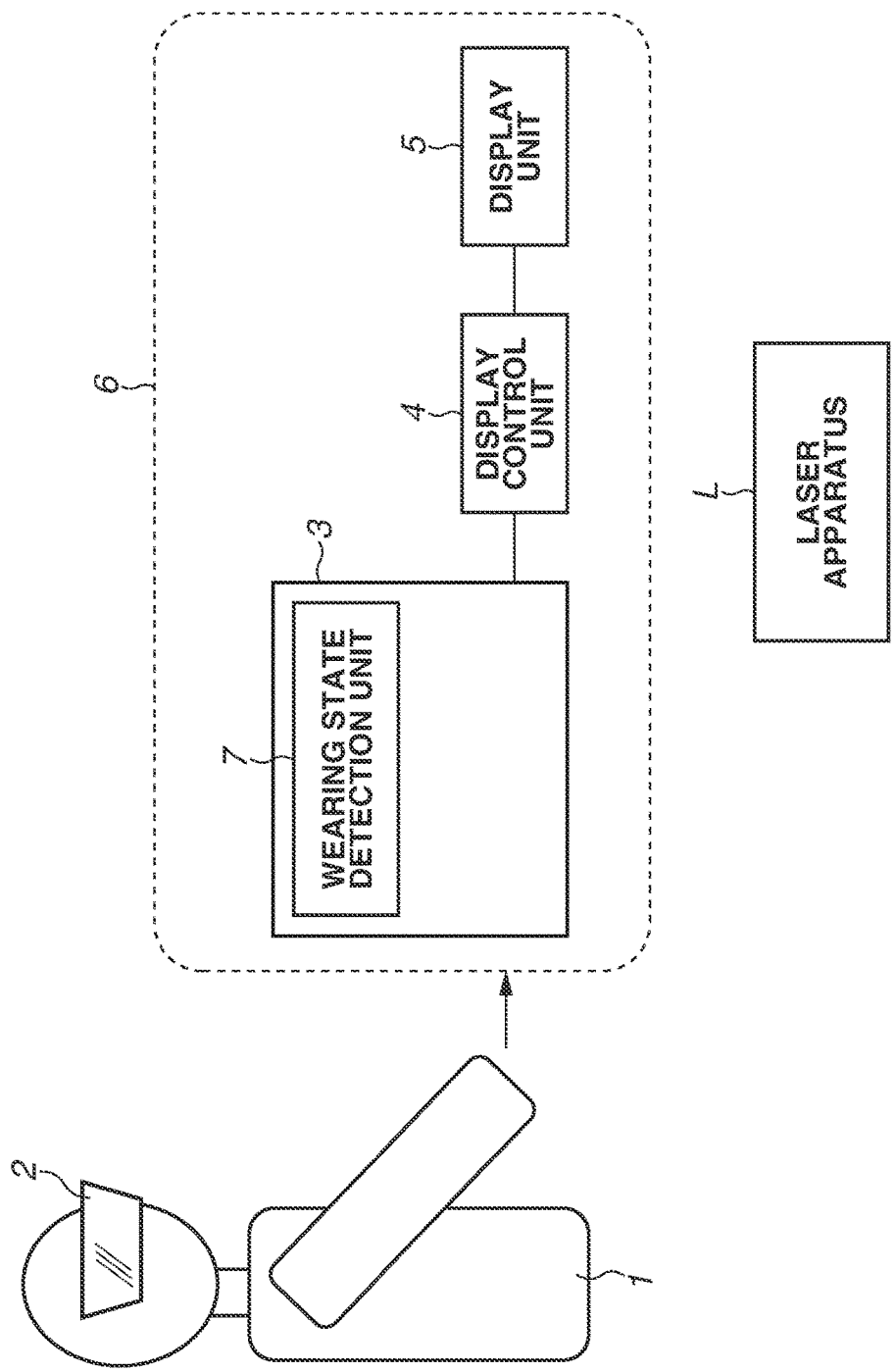
FIG. 6 is a schematic diagram illustrating a configuration of a display system according to an exemplary embodiment of the present disclosure.

FIG. 6 is a schematic diagram illustrating the configuration of the display system according to the present exemplary embodiment. A display system 6 according to the present exemplary embodiment at least has an eyewear 2, an information acquisition unit 3, a display control unit 4, a display unit 5, and a wearing state detection unit 7.

(Wearing State Detection Unit 7)

The wearing state detection unit 7 detects whether the operator 1 wears the eyewear 2. Then, the wearing state detection unit 7 sends information of the detection result to the display control unit 4.

As a technique for detecting whether the operator 1 wears the eyewear 2, a known machine learning technique can be used. More specifically, this technique is achieved by the following method. The wearing state detection unit 7 can be configured having a camera for capturing a two-dimensional image, such as an RGB camera, and an information processing unit. From a positive image in which the laser safety goggles are worn and a negative image in which the laser safety goggles are not worn, the information processing unit learns the state where the operator 1 wears the laser safety goggles. Then, the wearing state detection unit 7 detects the head of the operator 1 from image information obtained by the RGB camera. Then, according to the information learned in advance, the wearing state detection unit 7 can detect whether the operator 1 wears the laser safety goggles.

It is more beneficial that the camera of the wearing state detection unit 7 has one or more RGB cameras. It is more desirable that a camera image should be captured chronologically and successively. A "camera image" in the following example refers to chronologically successive images.

Further, by detecting that the operator 1 wears the eyewear 2, a process other than the process of changing at least one of the luminance of display and the color map may be performed. For example, only if it is determined that the operator 1 wears the eyewear 2, a laser apparatus L is enabled to emit laser, or a measuring apparatus such as a photoacoustic apparatus is enabled to start measurement.

Further, in this example, the state where the goggles are worn is detected by learning based on images. Alternatively, another method may be used. For example, an image of the goggles can be stored in advance in the apparatus, and a face image of the operator can be captured by the camera in such a manner that the positions of the eyes and the position of the face coincide between the two images. It may be detected, by an image processing method such as template matching, whether the wear is attached to an eye portion. Alternatively, any other method may be used so long as the method can determine whether the wear is worn.

Figure 7:
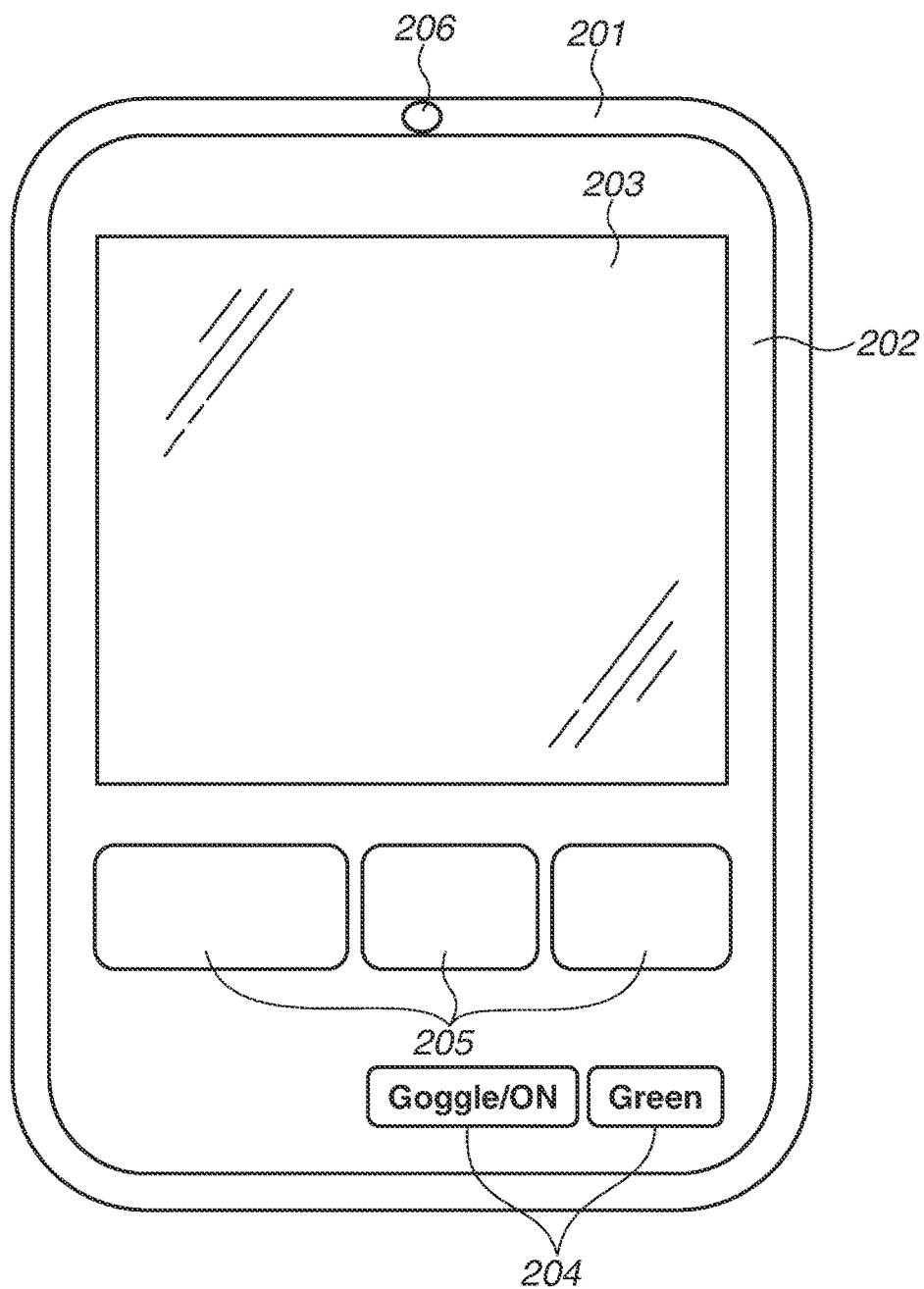
FIG. 7 is a schematic diagram illustrating a configuration of a display system according to an exemplary embodiment of the present disclosure.

With reference to FIG. 7, the information acquisition unit 3, the display control unit 4, the display unit 5, and the wearing state detection unit 7 are described on the assumption that the display system 6 is a tablet terminal. The tablet terminal illustrated in FIG. 7 is different from the tablet terminal illustrated in FIG. 4 in that the tablet terminal illustrated in FIG. 7 has an RGB camera 206 as the wearing state detection unit 7. The wearing state detection unit 7 detects the head of a human body in a captured camera image and extracts an image of a portion around the head. Based on the extracted image, the wearing state detection unit 7 detects, using laser safety goggle wearing information learned in advance, whether the operator 1 wears the laser safety goggles. As a result of the detection, if the operator 1 does not wear the laser safety goggles, the wearing state detection unit 7 performs nothing. If the operator 1 wears the laser safety goggles, the wearing state detection unit 7 transmits information of the detection result to the display control unit 4. The subsequent processes are similar to those in the first exemplary embodiment. In the present exemplary embodiment, the wearing state of the laser safety goggles is automatically acquired based on a camera image. Thus, the button on the left side of the UI 204 may not be provided. It is, however, desirable to prepare the button on the left side of the UI 204 in case detection based on the camera image does not function.

(Processing Flow)

Figure 8:
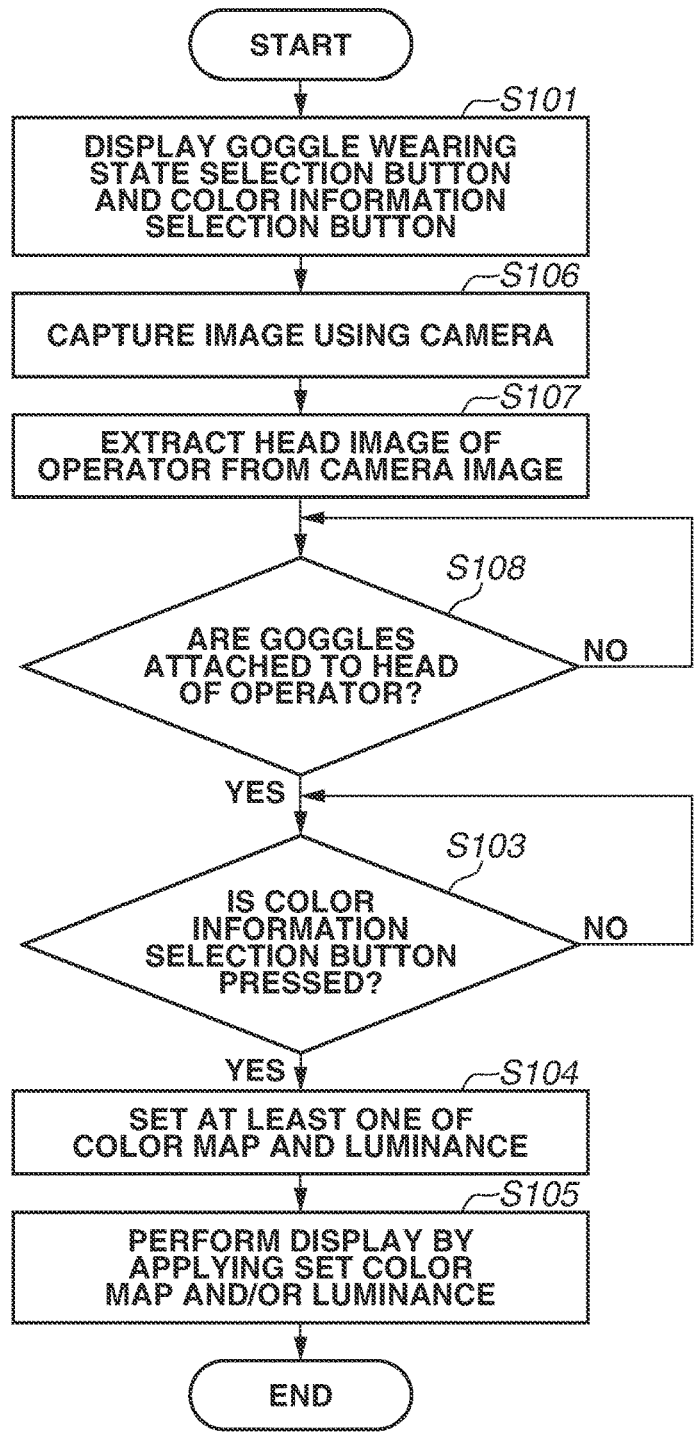
FIG. 8 is a flowchart illustrating a processing flow performed by a display system according to an exemplary embodiment of the present disclosure.

Next, the processing flow of the information acquisition unit 3, the display control unit 4, the display unit 5, and the wearing state detection unit 7 is described. FIG. 8 is a flowchart illustrating a processing flow according to the present exemplary embodiment. In this flowchart, the description is given on the assumption that a goggle wearing image is learned in advance.

In the processing flow illustrated in FIG. 8, the processes of steps designated by the same numerals as those in FIG. 2 are similar to those described in the first exemplary embodiment and therefore are not described in detail here.

In the present exemplary embodiment, after step S101, then in step S106, an image is captured by the camera that is the wearing state detection unit 7. As described above, the goggle wearing state selection button may not be displayed.

In step S107, the wearing information acquisition unit 3 extracts the head image of the operator 1 from the camera image captured in step S106.

In step S108, based on the image extracted in step S107, the wearing information acquisition unit 3 determines whether the laser safety goggles are attached to the head of the operator 1. If it is determined that the laser safety goggles are attached to the head of the operator 1 (YES in step S108), the processing proceeds to step S103. If not (NO in step S108), the process of step S108 is executed again.

The subsequent processes are similar to those in the first exemplary embodiment and therefore are not described here.

In a case where the goggle wearing state selection button is displayed as the UI 204, then in step S108, it may be determined whether at least one of the determination result based on the extracted image and the detection of the pressing of the goggle wearing state selection button is satisfied. In this manner, the wearing information acquisition unit 3 can acquire wearing information of the goggles based on either automatic determination by the display system 6 or specifying by the operator 1.

Further, the above description has been given taking as an example the configuration in which the operator inputs the color of the light transmission portion. Alternatively, the configuration may be such that the display system estimates the color of the light transmission portion from a camera image captured by the camera provided in the display system. In this manner, it is possible to improve the convenience of the display system. In this case, it is desirable to perform display urging the operator to confirm whether the color of the light transmission portion estimated by the display system is appropriate.

A more specific example of the second exemplary embodiment is described below. In the present example, the eyewear 2 is laser safety goggles including a green light transmission portion. The head of the operator 1 is captured by a camera attached to a mobile electronic tablet terminal as the display system 6, thereby determining whether the laser safety goggles are worn. Then, the types of laser safety goggles are displayed. The mobile electronic tablet terminal stores, with respect to each of a plurality of pairs of laser safety goggles, a color map having a finite number of colors taking into account the spectrum of the pair of laser safety goggles and the light emission spectrum of a display. If one of the types of laser safety goggles is selected, the color map of a display portion of the tablet terminal is changed according to a color map corresponding to the selected laser safety goggles. In the present example, the luminance is not set.

First, the camera attached to the mobile electronic tablet terminal enters a moving image capturing state. The operator wears the green laser safety goggles and captures the face of the operator themselves wearing the goggles, using the camera. Then, the tablet terminal detects that the operator wears the goggles. Next, the tablet terminal displays a list of the types of laser safety goggles that can be selected. If one of the types of laser safety goggles is selected, the color map of the display is changed using a color map corresponding to the selected goggles, thereby performing display. A color map is created using the light emission spectrum of the display and the transmission spectrum of the laser safety goggles. The HSV color space is divided into 10000 colors. Each color is multiplied by the light emission spectrum of the display, the transmission spectrum of the goggles, and the CIE standard color-matching functions. The same colors are removed from the resulting color map to extract 1000 colors. Using these 1000 colors, the color of a UI of the display system and the color of an image display portion are determined.

Consequently, it is possible to provide a technique for, if an operator wears an eyewear, detecting the wearing of the eyewear using a camera and an information processing unit, and changing the color map of a display system to a color map corresponding to the light emission spectrum of a display and the transmission spectrum of the eyewear, thereby performing display.

In this manner, when an operator wears an eyewear including a colored light transmission portion, such as laser safety goggles, it is possible to display a selection list of color maps on a display unit without the operator notifying a display system that the goggles are worn. Then, even if the operator views a UI of a tablet terminal through the light transmission portion, it is possible to reduce a decrease in the visibility occurring due to the mixture of colors and enable the operator to easily operate the UI of the tablet terminal.

A display system according to a third exemplary embodiment is a display system used in conjunction with an eyewear capable of detecting that an operator wears the eyewear and transmitting the detection result. Based on wearing information received from the eyewear, the display system sets the luminance of display and a color map according to the eyewear. In the display system according to the present exemplary embodiment, the eyewear is laser safety goggles including a pressure-sensitive sensor and a transmission unit. The pressure-sensitive sensor as a wearing state detection unit detects whether the eyewear is worn by the operator. The transmission unit can transmit, to the display system, information including the color of a light transmission portion of the laser safety goggles, spectrum information of transmitted light, and color map information after a change, in addition to wearing state information indicating the wearing state detected by the wearing state detection unit. Based on the information received from the eyewear, the display system can set at least one of the luminance and the color map of the display system.

According to the present exemplary embodiment, it is possible to reduce a decrease in the visibility occurring due to the mixture of colors and enable an operator to easily operate a UI of a tablet terminal.

FIG. 9 is a schematic diagram illustrating the configuration of the display system according to the present exemplary embodiment. A display system 6 according to the present exemplary embodiment has an information acquisition unit 3, a display control unit 4, and a display unit 5. The information acquisition unit 3 has a wear information reception unit 8, which receives information transmitted from an eyewear 2. Based on the received information, the display control unit 4 sets a color map and updates the display of the display unit 5.

In the following description, components such as the eyewear 2, the wear information reception unit 8, the display control unit 4, and the display unit 5 are described. Then, with reference to FIG. 11, the processing flow performed by the display system is described. Only the differences from the first and second exemplary embodiments are described below.

(Eyewear 2)

The eyewear 2 has a wearing state detection unit for detecting whether an operator 1 wears the eyewear 2, and a transmission unit for transmitting information of the eyewear 2 to the wear information reception unit 8. The information transmitted from the eyewear 2 has wearing information indicating the wearing state, information about the color of a light transmission portion, transmission spectrum information of the light transmission portion, and color map information to be set by the display control unit 4. These pieces of information are collectively referred to as "wear information".

The wearing state detection unit is configured having a detector, such as a pressure-sensitive sensor or an eyeball detection camera, for detecting whether the eyewear 2 is worn by an operator adequate to wear the eyewear 2. In a case where the detector is a pressure-sensitive sensor, it is desirable that the pressure-sensitive sensor should be placed at the position where the eyewear 2 comes into contact with the operator 1 when the operator 1 appropriately wears the eyewear 2. Alternatively, it may be detected by another technique whether the eyewear 2 is worn by an operator adequate to wear the eyewear 2. For example, pressure-sensitive sensors may be provided in portions that touch both ears. Then, when both pressure-sensitive sensors continue to stably detect pressure in a temporally continuous manner, it may be detected that the eyewear 2 is worn. Further, in a case where the detector is an eyeball detection camera, it is desirable that the camera should be provided at the position where the camera can detect human eyeballs when the operator 1 appropriately wears the eyewear 2. In a case where an operator to wear the eyewear 2 is identified in advance, the iris patterns of the eyes of the identified operator may be stored in advance in the eyewear 2 or the display system 6. The configuration may be such that only if the stored iris patterns match iris patterns acquired using the camera, the operation of the display system 6 is permitted. According to this configuration, it is possible to reduce the possibility that a person not permitted to operate the display system 6 uses the display system 6. Particularly, this is useful in a case where a laser apparatus L is controlled through the display system 6.

The transmission unit may be any transmission unit capable of transmitting wear information and may use wired communication or wireless communication.

Figure 10:
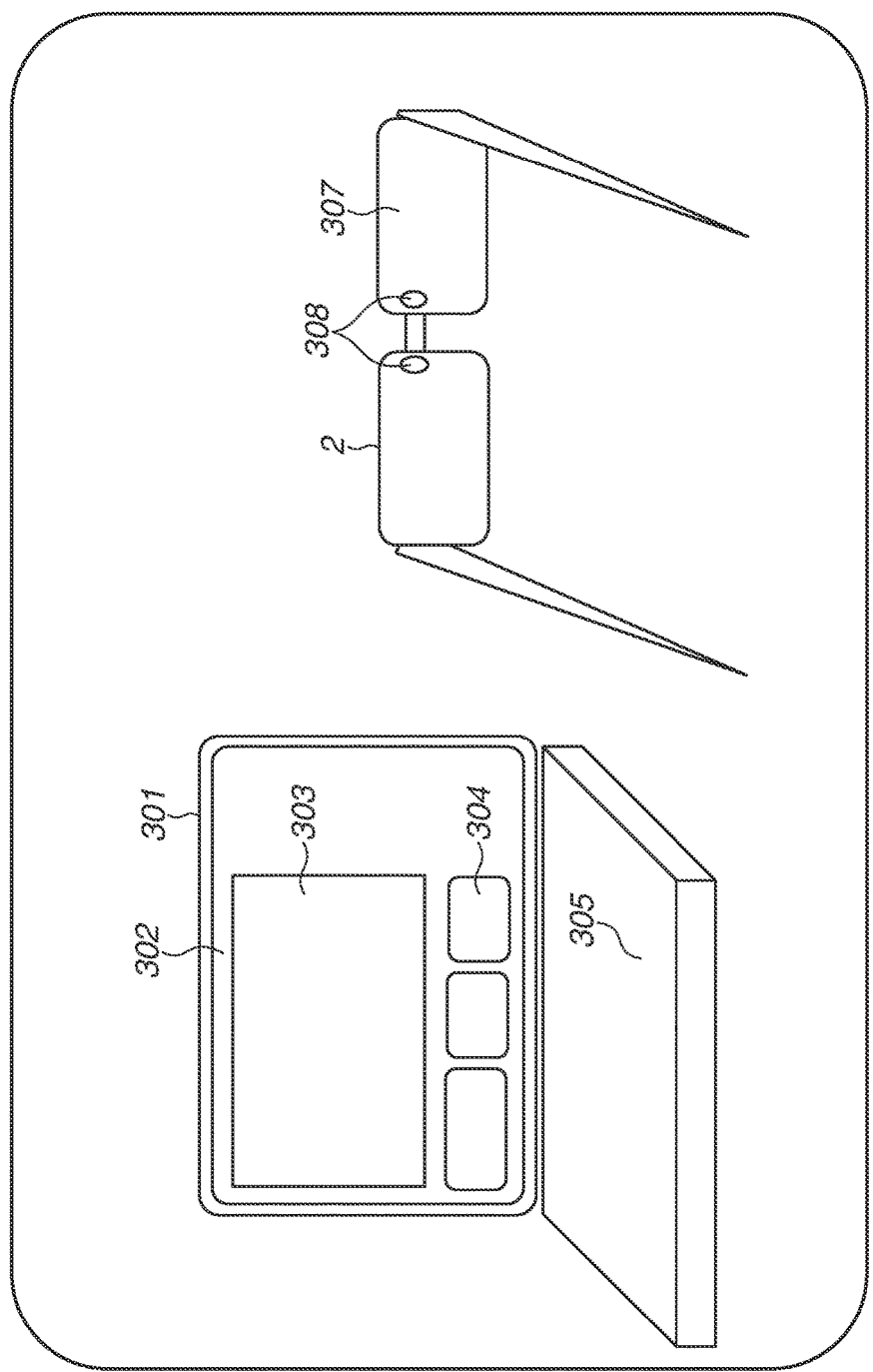
FIG. 10 is a schematic diagram illustrating a configuration of a display system according to an exemplary embodiment of the present disclosure.

FIG. 10 illustrates an example of the eyewear 2 according to the present exemplary embodiment. The eyewear has the structure of sunglasses and has a light transmission portion 307 and an eyeball detection camera 308. If the eyewear 2 is turned on, the eyeball detection camera 308 operates. If the operator 1 wears the eyewear 2, and the eyeball detection camera 308 detects eyeballs, the eyewear 2 determines that the eyewear 2 is worn. If it is determined that the operator 1 wears the eyewear 2, the transmission unit transmits information of the determination result to the wear information reception unit 8. The wear information reception unit 8 transmits the information to the display control unit 4.

(Wearing Information Acquisition Unit 3)

The wearing information acquisition unit 3 according to the present exemplary embodiment has the wear information reception unit 8, which receives wear information transmitted from the eyewear 2. The wearing information acquisition unit 3 transmits the received wear information to the display control unit 4. The reception device may be any reception device capable of receiving wear information and may use wired communication or wireless communication.

(Display Control Unit 4)

With reference to FIG. 10, a description is given on the assumption that the display system 6 according to the present exemplary embodiment is a portable personal computer. In FIG. 10, a portable personal computer 301, which is the display system 6, has a display unit 302, which is the display unit 5, and a keyboard 305. The portable personal computer 301 may have pointing devices such as a mouse and a trackball in addition to the keyboard 305. FIG. 10 illustrates the state where the display unit 302 displays a display area 303, where an image is displayed, and a UI 304. A case has been described where the wearing state of the eyewear 2 and the color information of the light transmission portion are selected through the UI 304 on a screen. Alternatively, the selection may be achieved in a hardware manner by assigning a key of the keyboard 305 or separately providing a dedicated switch for inputting the wearing state and the color information.

(Processing Flow)

Figure 11:
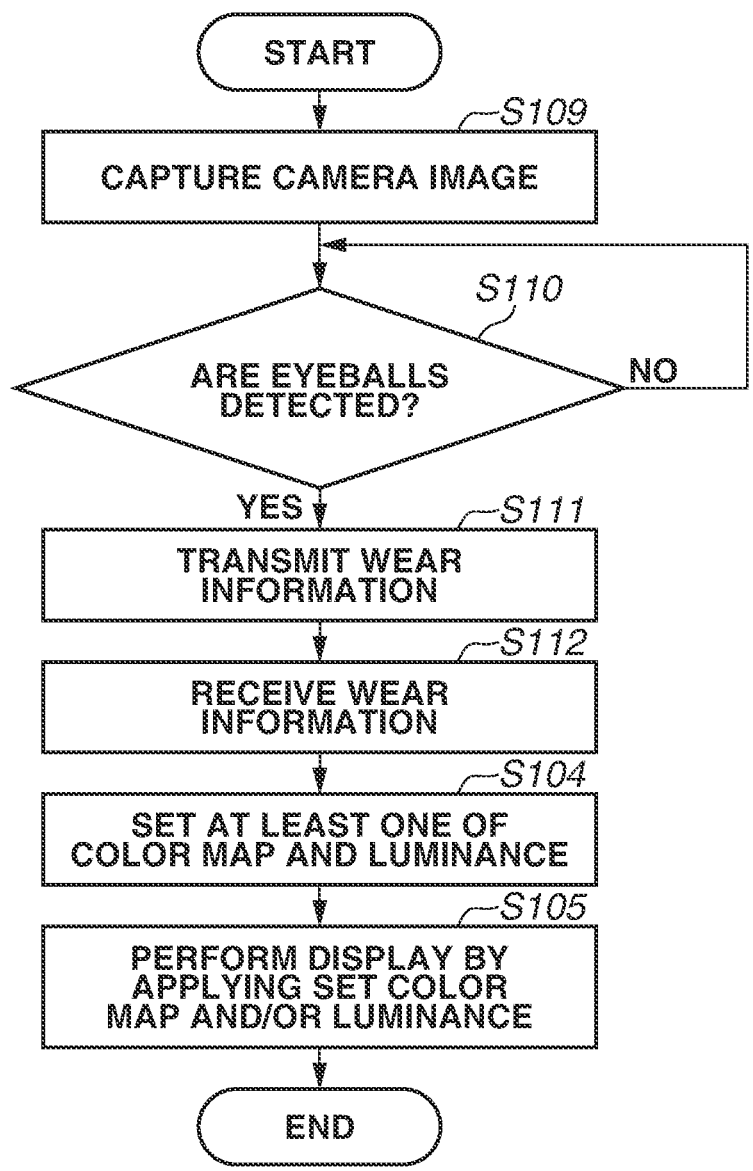
FIG. 11 is a flowchart illustrating a processing flow performed by a display system according to an exemplary embodiment of the present disclosure.

Next, with reference to FIG. 11, a processing flow according to the present exemplary embodiment is described. The description is given on the assumption that the wearing state detection unit is an eyeball detection camera, and when the flow is started, the eyewear 2 is already turned on, and eyeball detection is already started.

In step S109, a camera image is captured by the camera of the eyewear 2. Then, in step S110, it is determined whether eyeballs in the state where the eyewear is appropriately worn are detected from the captured camera image.

If eyeballs are detected (YES in step S110), the processing proceeds to step S111. If not (NO in step S110), the process of step S110 is repeated.

In step S111, the eyewear 2 transmits wear information such as wearing information indicating that the eyewear 2 is worn by the operator 1, and the color of the light transmission portion.

In step S112, the display system 6 receives the wear information. The subsequent processes are similar to those in the above exemplary embodiments and therefore are not described here. Similarly to the above exemplary embodiments, in a case where the display system 6 operates in conjunction with the laser apparatus L, the laser apparatus L may be operated according to the fact that it is detected that the eyewear 2 is worn. For example, only if it is determined that the eyewear 2 is worn, the laser apparatus L may be enabled to emit laser light, or in a case where the laser apparatus L is a measuring apparatus such as a photoacoustic apparatus, may be enabled to start measurement.

In FIG. 11, a description has been given on the assumption that steps S109 to S111 are performed by the eyewear 2. The present exemplary embodiment, however, is not limited to this. Alternatively, for example, a processing flow as illustrated in FIG. 12 may be employed.

In the processing flow illustrated in FIG. 12, in step S109, the eyewear 2 captures a camera image. Then, in step S113, the eyewear 2 transmits the captured camera image together with wear information to the display system 6. In step S114, if the display system 6 receives the camera image and the wear information, then in step S110, the information acquisition unit 3 determines whether eyeballs are detected from the camera image. In this case, the wearing information acquisition unit 3 has a determination unit for determining, based on the detection of eyeballs, whether the eyewear 2 is worn.

In this manner, the eyewear 2 does not need to perform the process of detecting eyeballs in the camera image. This can simplify the configuration of the eyewear 2. Also in a case where the wearing state detection unit is a pressure-sensitive sensor, the eyewear 2 may transmit the output of the pressure-sensitive sensor to the display system 6, and the display system 6 may determine whether the eyewear 2 is worn.

A more specific example of the present exemplary embodiment will be described. In the present example, the eyewear is laser safety goggles. Pressure-sensitive sensors are provided in temple portions and nose pad portions of the laser safety goggles, and a camera is provided near the nose pads. The pressure-sensitive sensors acquire pressure, and the camera captures an image of irises. Based on the determination results of pressure and irises, it is detected whether the laser safety goggles are worn by an operator permitted to use the laser safety goggles. Then, if it is determined that the laser safety goggles are worn by an operator permitted to use the laser safety goggles, it is possible to transmit information of the laser safety goggles to the display system and set a color map suitable for the laser safety goggles, thereby performing display. In the present example, the luminance is not set.

First, the camera and the pressure-sensitive sensors of the laser safety goggles are set to operating states. If the operator wears the laser safety goggles, the laser safety goggles detect that the laser safety goggles are worn by the operator. Then, the laser safety goggles transmit wear information about the laser safety goggles to the display system. Next, according to the received wear information, the display system sets the color map of a display using a color map corresponding to the laser safety goggles. If the color map is changed, display is performed by reflecting the change. A color map is created using the light emission spectrum of the display and the transmission spectrum of the laser safety goggles. The HSV color space is divided into 10000 colors. Each color is multiplied by the light emission spectrum of the display, the transmission spectrum of the laser safety goggles, and the CIE standard color-matching functions. The same colors are removed from the resulting color map to extract 1000 colors. Using these 1000 colors, the color of a UI of the display system and the color of an image display portion are determined.

In the present example, it is possible to provide the following technique. If an operator wears an eyewear, the eyewear detects the wearing of the eyewear and transmits wear information to a wear information reception unit. Then, based on the received eyewear information, a display system changes the color map of the display system to a color map corresponding to the color of the eyewear, thereby performing display.

In this manner, when an operator wears an eyewear capable of detecting the wearing of the eyewear, it is possible to set the luminance or the color map of a display in a hands-free manner. Also in the present example, even if the operator views a UI of a tablet terminal through the color of laser safety goggles, it is possible to reduce a decrease in the visibility occurring due to the mixture of colors and enable the operator to easily operate the UI of the tablet terminal.

A fourth exemplary embodiment will be described below. In the above exemplary embodiments, a case has been described where in addition to wearing information indicating the wearing state of the eyewear, information about the color of the light transmission portion of the eyewear is input to the information acquisition unit. Alternatively, the configuration may be such that information about the color of the light transmission portion of the eyewear is not input to the display system.

In a case where an eyewear to be worn by the operator is determined in advance, a color map to be applied when the eyewear is worn and a color map to be applied when the eyewear is not worn may be prepared. Based on wearing information indicating the wearing state of the eyewear, the display system may determine which of the color maps is to be applied. According to the present exemplary embodiment, it is possible to save the operator the trouble of inputting color information of the light transmission portion. Further, it is possible to reduce the capacity for storing color maps according to the colors of many transmission portions in the display system, and the time required for the display system to calculate these color maps. The same applies to the luminance.

In the present exemplary embodiment, the display system can acquire wearing information using a technique as described above in the other exemplary embodiments.

The present disclosure is also achieved by executing the following process. More specifically, the present disclosure can also be achieved by the process of supplying a program for achieving one or more functions of the above exemplary embodiments to a system or an apparatus via a network or a storage medium, and of causing one or more processors of a computer of the system or the apparatus to read and execute the program. Further, the present disclosure can also be achieved by a circuit (e.g., a field programmable gate array (FPGA) or an application-specific integrated circuit (ASIC)) for achieving one or more functions.

The display system according to each of the above exemplary embodiments sets at least one of the luminance and the color map of a display screen based on wearing information indicating the wearing state of an eyewear. More specifically, as a method for controlling a display system, at least one of the luminance and the color map of a display screen is set based on an input of wearing information of an eyewear.

In the display system according to the first exemplary embodiment, an operator themselves inputs wearing information to the display system. In the display system according to the second exemplary embodiment, the display system has an image capture unit as a wearing information acquisition unit and acquires wearing information of an eyewear based on a captured camera image. In the display system according to the third exemplary embodiment, the display system receives wearing information transmitted from an eyewear. In the fourth exemplary embodiment, wearing information may be acquired using any technique.

Further, the display system according to each of the first to third exemplary embodiments acquires, in addition to the wearing information, information about the color of a colored light transmission portion of the eyewear, and based on the information, sets at least one of the luminance and the color map of a display screen. The display system according to the fourth exemplary embodiment, in a case where an eyewear to be used by an operator is determined in advance, sets at least one of the luminance and the color map of a display screen based only on the wearing information.

The eyewear according to the third exemplary embodiment has a transmission unit for transmitting wearing information indicating the wearing state of the eyewear. Further, the eyewear may have a wearing detection unit such as an image capture unit or a pressure-sensitive sensor. Further, the eyewear may transmit information about the color of the light transmission portion in addition to the wearing information.

As described above, according to the exemplary embodiments of the present disclosure, when an operator wears an eyewear, and even if the operator views a display screen, it is possible to reduce a decrease in the visibility occurring due to the mixture of colors and enable the operator to easily operate a UI.

Even in a case where an operator wearing an eyewear views a display screen, it is possible to reduce a decrease in the visibility occurring due to the mixture of colors and enable the operator to easily operate a UI.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-007424, filed Jan. 18, 2016, which is hereby incorporated by reference herein in its entirety.

What is claimed is:

1. A display system comprising:
a display unit including a display screen; and
a display control unit,
wherein the display control unit sets at least one of luminance and a color map of the display screen based on wearing information indicating a wearing state of a plurality of eyewear, the wearing information being information indicating whether at least one of the plurality of eyewear is properly worn when the at least one of the plurality of eyewear is positioned over a wearer's eyes and the wearer's eyes are able to view the display unit through the worn eyewear, and wherein, in a case where the wearing information does not satisfy a predetermined criterion, the display control unit further displays on the display unit, an indication to prompt users of the plurality of eyewear to change one or more of the plurality of eyewear.

2. The display system according to claim 1, further comprising a wearing information acquisition unit configured to acquire the wearing information.

3. The display system according to claim 2, wherein the wearing information acquisition unit comprises an image capture unit, and wherein the wearing information acquisition unit acquires the wearing information based on an image captured by the image capture unit.

4. The display system according to claim 2, wherein, in a case where the at least one of the plurality of eyewear comprises a colored light transmission portion, the wearing information acquisition unit further acquires information about a color of the light transmission portion.

5. The display system according to claim 2, wherein the wearing information acquisition unit comprises a receiver configured to receive the wearing information from the plurality of eyewear.

6. The display system according to claim 2, wherein the wearing information acquisition unit further comprises an input unit configured to receive an input of the wearing information provided by an operator.

7. The display system according to claim 1, wherein the display system is configured as a tablet terminal.

8. The display system according to claim 1 further comprising a photoacoustic apparatus comprising a light source, wherein the display control unit allows the light source to emit light in a case where the wearing information of the plurality of eyewear satisfy a predetermined criterion.

9. The display system according to claim 1, wherein the display control unit sets the at least one of the luminance and the color map of the display screen further based on transmission spectra of the plurality of eyewear.

10. The display system according to claim 1, wherein the predetermined criterion is determined on a basis of a synthetic transmission spectrum of the plurality of the eyewear.

11. A method for controlling a display system having a display unit, the method comprising:

setting at least one of luminance and a color map of the display unit based on an input of wearing information indicating a wearing state of a plurality of eyewear, the wearing information being information indicating whether at least one of the plurality of eyewear is properly worn when the at least one of the plurality of eyewear is positioned over a wearer's eyes and the wearer's eyes are able to view the display unit through the worn eyewear, and displaying on the display unit, in a case where the wearing information does not satisfy a predetermined criterion, an indication to prompt users of the plurality of eyewear to change one or more of the plurality of eyewear.

12. The method for controlling the display system according to claim 11, further comprising:

prompting an operator to input the wearing state and input information about a color of a light transmission portion of the at least one of the plurality of eyewear.

13. The method for controlling the display system according to claim 12, further comprising:

after the wearing state is input, prompting the operator to input the information about the color of the light transmission portion of the at least one of the plurality of eyewear.

14. The method for controlling the display system according to claim 11, wherein the wearing state of the plurality of eyewear is determined based on an image captured by an image capture unit.

15. The method for controlling the display system according to claim 11, wherein information about a color of a light transmission portion of the at least one of the plurality of eyewear is acquired based on an image captured by an image capture unit.

16. The method for controlling the display system according to claim 11, wherein at least one of the luminance and the color map of the display unit is set based on the wearing state and information about a color of a light transmission portion of the at least one of the plurality of eyewear input via the at least one of the plurality of eyewear.

17. The method for controlling the display system according to claim 11, wherein an operator is prompted to select the color map to be set from among a plurality of color maps.

18. The method for controlling the display system according to claim 11, wherein, in a case where it is determined that the at least one of the plurality of eyewear is worn by an operator, a signal permitting emission of laser light from a laser light source is transmitted to a measuring apparatus that comprises the laser light source and that operates in conjunction with the display system.

19. The method for controlling the display system according to claim 18, wherein the measuring apparatus is a photoacoustic apparatus.

20. The method according to claim 11, wherein the setting is performed further based on transmission spectra of the plurality of eyewear.

21. The method according to claim 11, wherein the predetermined criterion is determined on a basis of a synthetic transmission spectrum of the plurality of the eyewear.

* * * * *